US008594802B2

(12) United States Patent
Stahmann et al.

(10) Patent No.: US 8,594,802 B2
(45) Date of Patent: Nov. 26, 2013

(54) PERFORMANCE ASSESSMENT AND ADAPTATION OF AN ACOUSTIC COMMUNICATION LINK

(71) Applicant: Cardiac Pacemakers, Inc., St. Paul, MN (US)

(72) Inventors: Jeffrey E. Stahmann, Ramsey, MN (US); Keith R. Maile, New Brighton, MN (US); Paul J. Huelskamp, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/781,476

(22) Filed: Feb. 28, 2013

(65) Prior Publication Data
US 2013/0178909 A1   Jul. 11, 2013

Related U.S. Application Data

(63) Continuation of application No. 13/349,681, filed on Jan. 13, 2012, now Pat. No. 8,401,662, which is a continuation of application No. 12/497,183, filed on Jul. 2, 2009, now Pat. No. 8,126,566.

(60) Provisional application No. 61/088,891, filed on Aug. 14, 2008.

(51) Int. Cl.
*A61N 1/00*     (2006.01)
(52) U.S. Cl.
USPC .......................................................... 607/60
(58) Field of Classification Search
USPC ....................................................... 607/60, 3
See application file for complete search history.

(56) References Cited

U.S. PATENT DOCUMENTS

| | | | |
|---|---|---|---|
| 3,672,352 A | 6/1972 | Summers | |
| 4,361,153 A | 11/1982 | Slocum et al. | |
| 4,373,527 A | 2/1983 | Fischell | |
| 4,481,950 A | 11/1984 | Duggan | |
| 4,519,401 A | 5/1985 | Ko et al. | |
| 4,573,994 A | 3/1986 | Fischell et al. | |
| 4,614,192 A | 9/1986 | Imran et al. | |

(Continued)

FOREIGN PATENT DOCUMENTS

| | | |
|---|---|---|
| EP | 0300552 | 1/1989 |
| JP | 03-034196 | 2/1991 |

(Continued)

OTHER PUBLICATIONS

International Search Report and Written Opinion issued in PCT/US2009/049552, mailed Jan. 28, 2010, 12 pages.

*Primary Examiner* — Robert N Wieland
(74) *Attorney, Agent, or Firm* — Faegre Baker Daniels LLP

(57) ABSTRACT

Systems and methods for adapting the performance of a wireless communication link with an implantable medical device (IMD) are disclosed. An illustrative method includes initiating a wireless link with the IMD, measuring an initial performance of the wireless link, determining whether the initial performance of the wireless link is adequate, adjusting an operating parameter related to the wireless link in the event the initial performance of the wireless link is inadequate, measuring a performance of the wireless link in response to the adjusted operating parameter, and setting the operating parameter to a prior setting if the measured performance of the wireless link does not improve in response to the adjusted operating parameter.

17 Claims, 6 Drawing Sheets

(56) References Cited

U.S. PATENT DOCUMENTS

| | | |
|---|---|---|
| 4,616,640 A | 10/1986 | Kaali et al. |
| 4,651,740 A | 3/1987 | Schroeppel |
| 4,793,825 A | 12/1988 | Benjamin et al. |
| 5,113,859 A | 5/1992 | Funke |
| 5,423,334 A | 6/1995 | Jordan |
| 5,713,939 A | 2/1998 | Nedungadi et al. |
| 5,733,313 A | 3/1998 | Barreras, Sr. et al. |
| 5,778,882 A | 7/1998 | Raymond et al. |
| 5,800,478 A | 9/1998 | Chen et al. |
| 5,814,089 A | 9/1998 | Stokes et al. |
| 5,833,603 A | 11/1998 | Kovacs et al. |
| 6,140,740 A | 10/2000 | Porat et al. |
| 6,141,588 A | 10/2000 | Cox et al. |
| 6,162,238 A | 12/2000 | Kaplan et al. |
| 6,164,284 A | 12/2000 | Schulman et al. |
| 6,170,488 B1 | 1/2001 | Spillman, Jr. et al. |
| 6,185,452 B1 | 2/2001 | Schulman et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,277,078 B1 | 8/2001 | Porat et al. |
| 6,308,099 B1 | 10/2001 | Fox et al. |
| 6,336,903 B1 | 1/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,431,175 B1 | 8/2002 | Penner et al. |
| 6,440,066 B1 | 8/2002 | Bardy |
| 6,442,413 B1 | 8/2002 | Silver |
| 6,442,433 B1 | 8/2002 | Linberg |
| 6,445,953 B1 | 9/2002 | Bulkes et al. |
| 6,453,196 B1 | 9/2002 | Von Arx et al. |
| 6,456,602 B1 | 9/2002 | Hwang et al. |
| 6,456,883 B1 | 9/2002 | Torgerson et al. |
| 6,472,991 B1 | 10/2002 | Schulman et al. |
| 6,571,128 B2 | 5/2003 | Lebel et al. |
| 6,628,989 B1 | 9/2003 | Penner et al. |
| 6,638,231 B2 | 10/2003 | Govari et al. |
| 6,654,638 B1 | 11/2003 | Sweeney |
| 6,675,049 B2 | 1/2004 | Thompson et al. |
| 6,712,772 B2 | 3/2004 | Cohen et al. |
| 6,764,446 B2 | 7/2004 | Wolinsky et al. |
| 6,783,499 B2 | 8/2004 | Schwartz |
| 6,792,311 B2 | 9/2004 | Fox et al. |
| 6,809,507 B2 | 10/2004 | Morgan et al. |
| 6,823,031 B1 | 11/2004 | Tatem, Jr. |
| 6,840,956 B1 | 1/2005 | Wolinsky et al. |
| 6,855,115 B2 | 2/2005 | Fonseca et al. |
| 6,895,265 B2 | 5/2005 | Silver |
| 6,907,285 B2 | 6/2005 | Denker et al. |
| 6,978,182 B2 | 12/2005 | Mazar et al. |
| 6,985,773 B2 | 1/2006 | Von Arx et al. |
| 7,003,350 B2 | 2/2006 | Denker et al. |
| 7,018,336 B2 | 3/2006 | Enegren et al. |
| 7,024,248 B2 | 4/2006 | Penner et al. |
| 7,027,871 B2 | 4/2006 | Burnes et al. |
| 7,033,322 B2 | 4/2006 | Silver |
| 7,061,381 B2 | 6/2006 | Forcier et al. |
| 7,134,999 B2 | 11/2006 | Brauker et al. |
| 7,187,979 B2 | 3/2007 | Haubrich et al. |
| 7,198,603 B2 | 4/2007 | Penner et al. |
| 7,214,189 B2 | 5/2007 | Zdeblick |
| 7,236,821 B2 | 6/2007 | Cates et al. |
| 7,273,454 B2 | 9/2007 | Raymond et al. |
| 7,273,457 B2 | 9/2007 | Penner |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 7,525,298 B2 | 4/2009 | Morgan et al. |
| 7,532,933 B2 | 5/2009 | Hastings et al. |
| 7,908,334 B2 | 3/2011 | Huelskamp et al. |
| 8,041,431 B2 | 10/2011 | Huelskamp et al. |
| 8,126,566 B2 | 2/2012 | Stahmann et al. |
| 2001/0043514 A1 | 11/2001 | Kita |
| 2002/0042561 A1 | 4/2002 | Schulman et al. |
| 2002/0045812 A1 | 4/2002 | Ben-Haim et al. |
| 2002/0065540 A1 | 5/2002 | Lebel et al. |
| 2002/0151770 A1 | 10/2002 | Noll, III et al. |
| 2002/0183628 A1 | 12/2002 | Reich et al. |
| 2003/0009204 A1 | 1/2003 | Amundson et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0195581 A1 | 10/2003 | Meadows et al. |
| 2004/0057340 A1 | 3/2004 | Charles-Erickson et al. |
| 2004/0064133 A1 | 4/2004 | Miller et al. |
| 2004/0088009 A1 | 5/2004 | Degroot |
| 2004/0152999 A1 | 8/2004 | Cohen et al. |
| 2005/0056539 A1 | 3/2005 | Morgan et al. |
| 2005/0159789 A1 | 7/2005 | Brockway et al. |
| 2005/0187482 A1 | 8/2005 | O'Brien et al. |
| 2005/0215887 A1 | 9/2005 | Ben-Haim et al. |
| 2005/0242479 A1 | 11/2005 | Petisce et al. |
| 2006/0004263 A1 | 1/2006 | Feliss et al. |
| 2006/0009818 A1 | 1/2006 | Von Arx |
| 2006/0030903 A1 | 2/2006 | Seeberger et al. |
| 2006/0031378 A1 | 2/2006 | Vallapureddy et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0122667 A1 | 6/2006 | Chavan et al. |
| 2006/0136004 A1 | 6/2006 | Cowan et al. |
| 2007/0053513 A1* | 3/2007 | Hoffberg .................. 380/201 |
| 2007/0142728 A1 | 6/2007 | Penner et al. |
| 2007/0208261 A1 | 9/2007 | Maniak et al. |
| 2008/0021333 A1 | 1/2008 | Huelskamp |
| 2008/0021972 A1 | 1/2008 | Huelskamp et al. |
| 2008/0082146 A1 | 4/2008 | Gandhi et al. |
| 2008/0112885 A1* | 5/2008 | Okunev et al. ............ 424/9.1 |
| 2008/0114224 A1 | 5/2008 | Brandy et al. |
| 2008/0129457 A1 | 6/2008 | Ritter et al. |
| 2008/0191581 A9 | 8/2008 | Penner et al. |
| 2008/0288038 A1 | 11/2008 | Paul et al. |
| 2008/0294208 A1* | 11/2008 | Willis et al. ................. 607/3 |
| 2008/0312719 A1 | 12/2008 | Keilman |
| 2009/0074216 A1 | 3/2009 | Bradford et al. |
| 2009/0075687 A1 | 3/2009 | Hino et al. |
| 2009/0177251 A1 | 7/2009 | Huelskamp et al. |
| 2009/0198307 A1 | 8/2009 | Mi et al. |
| 2010/0042177 A1 | 2/2010 | Stahmann et al. |
| 2011/0160804 A1 | 6/2011 | Penner |

FOREIGN PATENT DOCUMENTS

| | | |
|---|---|---|
| JP | 10-055202 | 2/1998 |
| WO | WO 99/34453 | 7/1999 |
| WO | WO 99/34731 | 7/1999 |
| WO | WO 2004/089465 | 10/2004 |
| WO | WO 2006/045073 | 4/2006 |
| WO | WO2006/045074 | 4/2006 |
| WO | WO 2006/045075 | 4/2006 |
| WO | WO 2006/069215 | 6/2006 |
| WO | WO 2007/070794 | 6/2007 |
| WO | WO 2008/011592 | 1/2008 |
| WO | WO 2008/011593 | 1/2008 |
| WO | WO 2008/060197 | 5/2008 |
| WO | WO 2009102640 | 8/2009 |

* cited by examiner

PERFORMANCE ASSESSMENT AND ADAPTATION OF AN ACOUSTIC COMMUNICATION LINK

CROSS-REFERENCE TO RELATED APPLICATIONS

This application is a continuation of U.S. application Ser. No. 13/349,681, filed Jan. 13, 2012, now U.S. Pat. No. 8,401,662, issued Mar. 19, 2013 entitled "Performance Assessment and Adaptation of an Acoustic Communication Link," which is a continuation of U.S. application Ser. No. 12/497,183, filed Jul. 2, 2009, now U.S. Pat. No. 8,126,566, issued Feb. 28, 2012, entitled "Performance Assessment and Adaptation of an Acoustic Communication Link," which claims priority under 35 U.S.C. §119 to U.S. Provisional Application No. 61/088,891, filed on Aug. 14, 2008, entitled "Performance Assessment And Adaptation of an Acoustic Communication Link," the disclosure of each of which is incorporated herein by reference in their entirety for all purposes.

TECHNICAL FIELD

The present invention relates generally to implantable medical devices. More particularly, the present invention relates to systems and methods for adapting a wireless communication link with an implantable medical device.

BACKGROUND

Implantable medical devices (IMDs) such as pacemakers and implantable cardioverter defibrillators are utilized in monitoring and regulating various conditions within the body. An implantable cardioverter defibrillator, for example, may be utilized in cardiac rhythm management applications to monitor the rate and rhythm of the heart and for delivering various therapies such as cardiac pacing, cardiac defibrillation, and/or cardiac therapy. In some cases, the IMD can be configured to sense various physiological parameters occurring within the body to determine the occurrence of any abnormalities in the operation of the patient's heart. Based on these sensed parameters, the IMD may then deliver an appropriate treatment to the patient.

Communication with IMDs is sometimes accomplished via a wireless telemetry link between an external device and the IMD, or between the IMD and another device located within the body. In some cases, ultrasonic transducers can be used to establish an acoustic link with the IMD, allowing data, operational status, and other information to be wirelessly transmitted through the body via an acoustic signal. Establishing and maintaining an acoustic link between the IMD and the communicating device is often difficult, however, based on the acoustic path between the IMD and the communicating device. In some cases, for example, the acoustic link can be compromised by the presence of body organs, vessels, airways, and other anatomical structures within the body. Factors that can affect the performance of the acoustic link can include the implant location of the IMD within the body, the orientation of the IMD within the body, the presence of physiological noise (e.g., heart sounds, vibration, etc.) within the body, and the presence of body tissue interfaces or other areas where there is an abrupt change in acoustic impedance that can cause reflections and absorption of the acoustic signal.

SUMMARY

The present invention relates to methods and systems for adapting a wireless communication link with an implantable medical device. An illustrative method of adapting the performance of a wireless communication link includes initiating a wireless link with the implantable medical device, measuring an initial performance of the wireless link, determining whether the initial performance of the wireless link is adequate, adjusting at least one operating parameter related to the wireless link in the event the initial performance of the wireless link is inadequate, measuring a performance of the wireless link in response to the adjusted operating parameter, and setting the operating parameter to a previous setting if the measured performance of the wireless link does not improve in response to the adjusted operating parameter.

A system in accordance with an exemplary embodiment includes an implantable medical device equipped with a physiological sensor and an acoustic transducer adapted to transmit and receive acoustic signals, a communicating device in acoustic communication with the implantable medical device via an acoustic link, and a processor adapted to adjust at least one operating parameter of the implantable medical device and/or the communicating device in response to a measured performance parameter of the acoustic link. In some embodiments, the communicating device comprises an external device having an acoustic transducer that transmits and receives acoustic signals to and from the implantable medical device. In other embodiments, the communicating device comprises another implanted device that transmits and receives acoustic signals to and from the implantable medical device. In one embodiment, the implantable medical device comprises a remote device having a pressure sensor adapted to sense blood pressure within a body vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
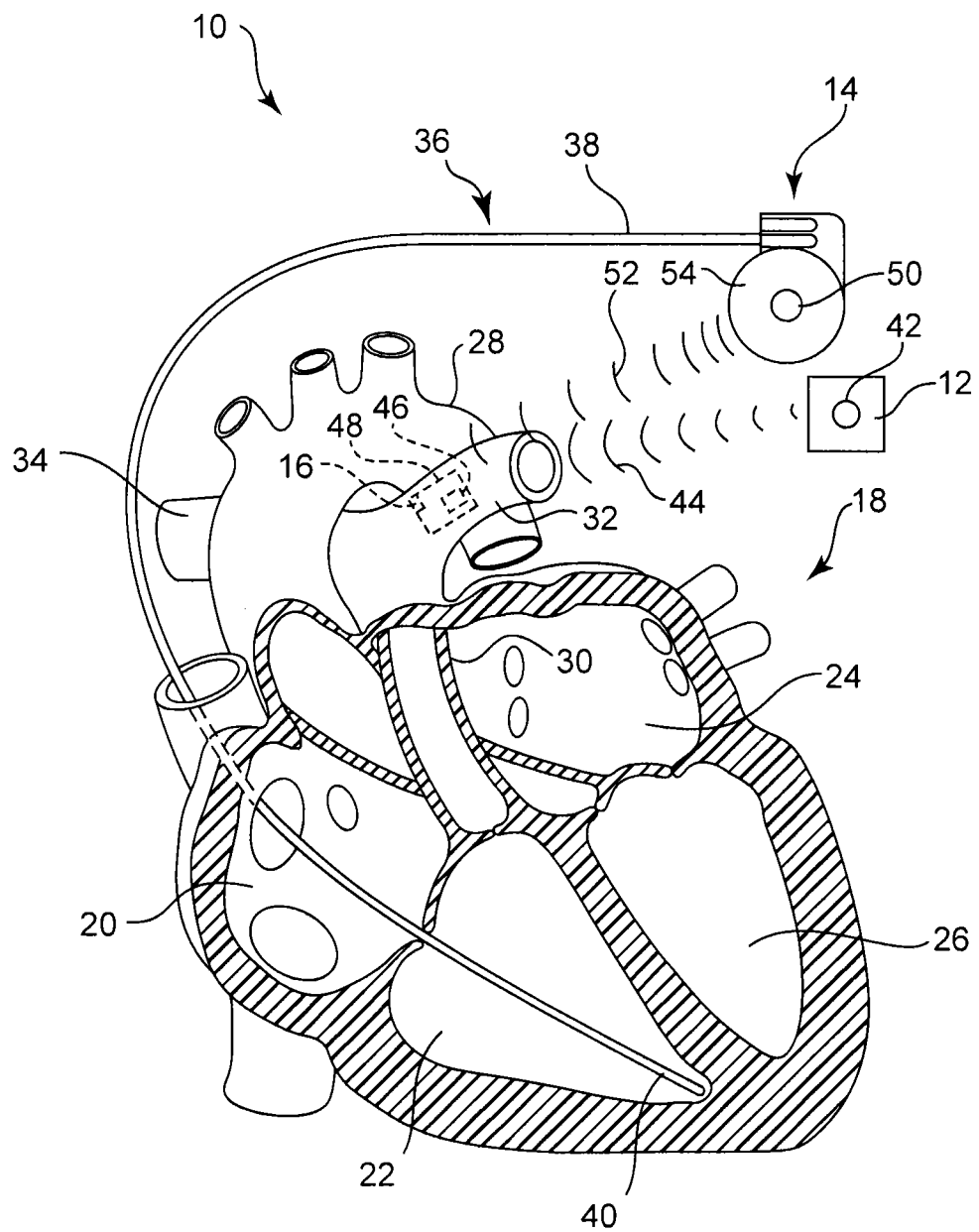
FIG. 1 is a schematic view of an illustrative system employing a remote implantable medical device located within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 employing a remote implantable medical device (IMD)

located within the body of a patient. The system 10, illustratively a cardiac rhythm management system for providing cardiac rhythm management to a patient, includes an external monitor 12 (e.g., an external wand or programmer), a pulse generator 14 implanted within the body at a location below the patient's skin, and at least one remote IMD 16 implanted deeply within the patient's body such as in one of the arteries or ventricles of the patient's heart 18. The heart 18 includes a right atrium 20, a right ventricle 22, a left atrium 24, a left ventricle 26, and an aorta 28. The right ventricle 22 leads to the main pulmonary artery 30 and the branches 32,34 of the main pulmonary artery 30. Typically, the pulse generator 14 will be implanted at a location adjacent to the location of the external monitor 12, which may lie adjacent to the exterior surface of the patient's skin.

In the illustrative system 10 depicted, the pulse generator 14 is coupled to a lead 36 deployed in the patient's heart 18. The pulse generator 14 can be implanted subcutaneously within the body, typically at a location such as in the patient's chest or abdomen, although other implantation locations are possible. A proximal portion 38 of the lead 36 can be coupled to or formed integrally with the pulse generator 14. A distal portion 40 of the lead 36, in turn, can be implanted at a desired location within the heart 18 such as the right ventricle 22, as shown. Although the illustrative system 10 depicts only a single lead 36 inserted into the patient's heart 18, it should be understood, however, that the system 10 may include multiple leads so as to electrically stimulate other areas of the heart 18. In some embodiments, for example, the distal portion of a second lead (not shown) may be implanted in the right atrium 20. In addition, or in lieu, another lead may be implanted in the left side of the heart 18 (e.g., in the coronary veins) to stimulate the left side of the heart 18. Other types of leads such as epicardial leads may also be utilized in addition to, or in lieu of, the lead 36 depicted in FIG. 1.

During operation, the lead 36 is configured to convey electrical signals between the heart 18 and the pulse generator 14. For example, in those embodiments where the pulse generator 14 is a pacemaker, the lead 36 can be utilized to deliver electrical therapeutic stimulus for pacing the heart 18. In those embodiments where the pulse generator 14 is an implantable cardiac defibrillator, the lead 36 can be utilized to deliver electric shocks to the heart 18 in response to an event such as a ventricular fibrillation. In some embodiments, the pulse generator 14 includes both pacing and defibrillation capabilities.

The remote IMD 16 can be configured to perform one or more designated functions, including the sensing of one or more physiological parameters within the body. Example physiological parameters that can be measured using the remote IMD 16 can include, but are not limited to, blood pressure, blood flow, temperature, and strain. Various electrical, chemical, magnetic, and/or sound properties may also be sensed within the body via the remote IMD 16. In one embodiment, the remote IMD 16 is adapted to deliver a desired therapy (e.g., a pacing and/or defibrillation stimulus) to the patient's heart 18 or cardiovascular system.

In the embodiment of FIG. 1, the remote IMD 16 comprises a pressure sensor implanted at a location deep within the body such as in the main pulmonary artery 30 or a branch 32,34 of the main pulmonary artery 30 (e.g., in the right or left pulmonary artery). An exemplary pressure sensor suitable for use in sensing pulmonary arterial pressure is described in U.S. Pat. No. 6,764,446, entitled "Implantable Pressure Sensors and Methods for Making and Using Them," which is incorporated herein by reference in its entirety for all purposes. In use, the remote IMD 16 can be used to aid in the prediction of heart decompensation of a heart failure patient and/or to aid in optimizing pacing and/or defibrillation therapy via the pulse generator 14 by taking pressure measurements within the body. In some embodiments, the remote IMD 16 can be configured to sense, detect, measure, calculate, and/or derive other associated parameters such as flow rate, maximum and minimum pressure, peak-to-peak pressure, rms pressure, and/or pressure rate change. For example, in some embodiments, the pressure signal from the remote IMD 16 can be used to detect changes in arterial blood pressure during a cardiac cycle or across multiple cardiac cycles.

The remote IMD 16 may be implanted in other regions of the patient's vasculature, in other body lumens, or in other areas of the body, and may comprise any type of chronically implanted device adapted to deliver therapy and/or monitor biological and chemical parameters, properties, and functions. The remote IMD 16 can be tasked, either alone or with other implanted or external devices, to provide various therapies within the body. In certain embodiments, for example, the remote IMD 16 may comprise a glucose level sensor that can be used in conjunction with an insulin pump for providing insulin treatment to the patient. Although a single remote IMD 16 is depicted in FIG. 1, multiple such devices could be implanted at various locations within the body for sensing physiologic parameters and/or providing therapy at multiple regions within the body.

An acoustic communication link may be established to permit wireless communications between the remote IMD 16 and the external device 12, between the remote IMD 16 and the pulse generator 14, and/or between the remote IMD 16 and another communicating device located inside or outside of the body. In the illustrative system 10 of FIG. 1, for example, the external device 12 includes an acoustic transducer 42 adapted to transmit an acoustic signal 44 into the body for establishing an acoustic link between the remote IMD 16 and the external device 12.

An acoustic transducer 46 coupled to the housing 48 of the remote IMD 16 is configured to receive the acoustic signal 44 transmitted by the external device 12. An example acoustic transducer suitable for use with the remote IMD 16 is described in U.S. Pat. No. 6,140,740, entitled "Piezoelectric Transducer," which is expressly incorporated herein by reference in its entirety for all purposes. In some embodiments, the transmission of the acoustic signal 44 to the remote IMD 16 can be used to activate the IMD 16 from a low-power, sleep state to an active, energized state. In one embodiment, for example, the acoustic signal 44 generated by the external device 12 can be used to wake up the remote IMD 16 from an initial, low-power state to an active state to take one or more sensor readings within the body and then transmit those readings to the external device 12, to the pulse generator 14, and/or to another device located inside or outside of the body.

In some embodiments, the acoustic signal 44 can be used to provide power to the remote IMD 16 and/or to recharge an energy storage device within the IMD 16 such as a rechargeable battery or power capacitor. In some embodiments, the acoustic signal 44 provides acoustical energy that can be converted into electrical energy to provide therapy to the patient, if desired.

While the system 10 of FIG. 1 includes an external device 12 in acoustic communication with a remote IMD 16, in other embodiments the system 10 may employ other devices located inside or outside of the patient's body that acoustically communicate with the IMD 16. As further shown in FIG. 1, for example, the pulse generator 14 can also include an acoustic transducer 50 adapted to transmit an acoustic signal 52 to the remote IMD 16 to establish an acoustic link between the pulse generator 14 and the remote IMD 16. In certain embodiments, the acoustic transducer 50 is coupled to an interior portion of the can 54 that encloses the various components of the pulse generator 14. In other embodiments, the acoustic transducer 50 is located outside of the can 54, or is coupled to the pulse generator 14 through a feedthrough provided on the can 54.

Although the system 10 depicted in FIG. 1 shows an acoustic link between the external device 12 and the remote IMD 16, and further between the IMD 16 and the pulse generator 14, in other embodiments an acoustic link can be established between the remote IMD 16 and another device implanted within the body. In some embodiments, for example, an acoustic communication link can be established between a primary IMD 16 and one or more secondary IMDs 16 implanted within the body.

While the illustrative system 10 utilizes acoustic transducers to wirelessly transfer data, control mode/function, operational parameters, and other information to and from the remote IMD 16, other modes of wireless communication are also possible. Examples of other wireless modes of communication can include, but are not limited to, radio frequency (RF), inductive, magnetic, or optical. In certain embodiments, several different modes of wireless communication can be utilized to wirelessly transmit information through the body. In one such embodiment, for example, an acoustic communication link is used to establish wireless communications between the remote IMD 16 and the external device 12, and an RF or inductive communication link is used to establish wireless communications between the pulse generator 14 and the external device 12. Other combinations of wireless communication modes are also possible.

Figure 2:
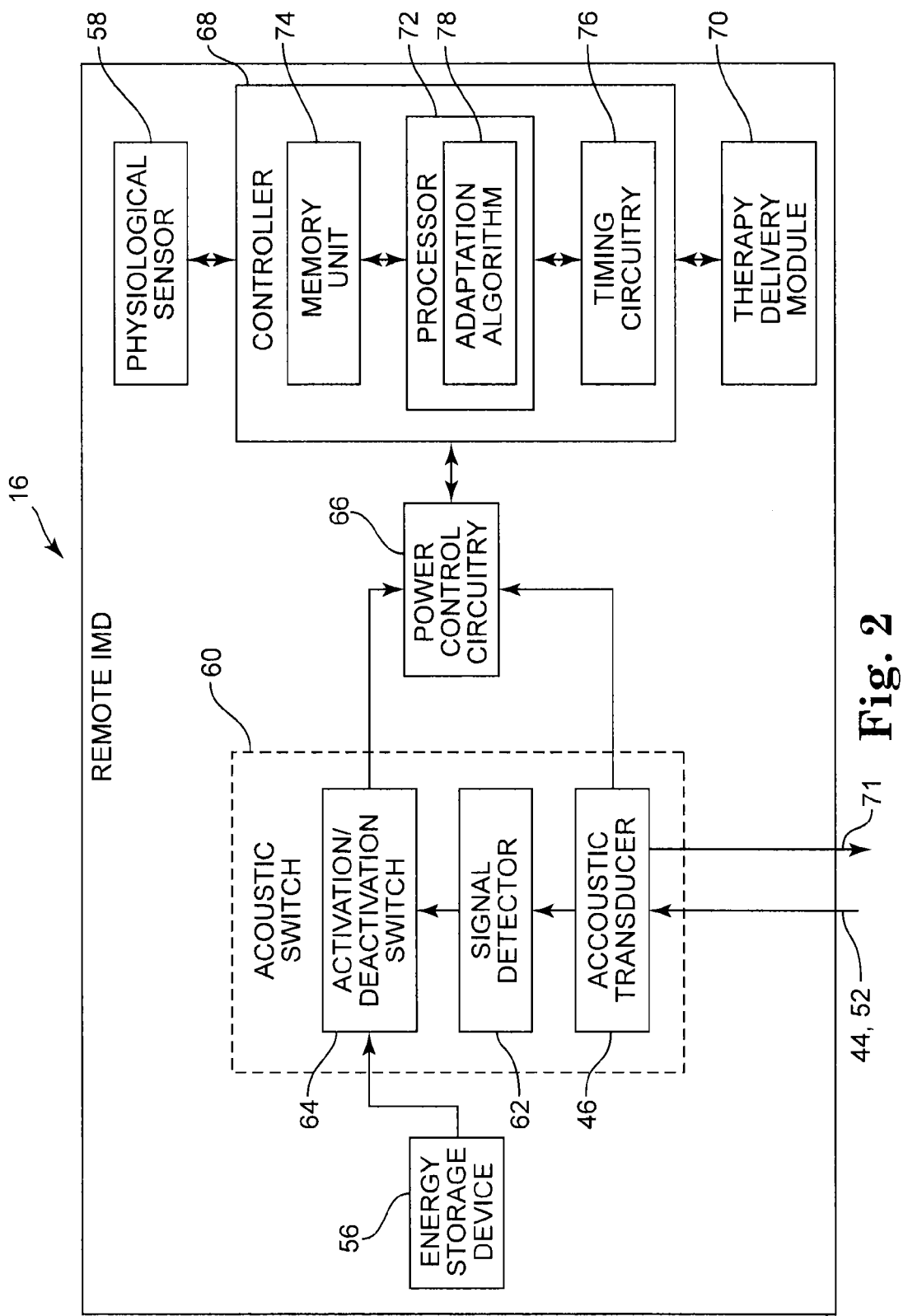
FIG. 2 is a block diagram of an illustrative embodiment of the implantable medical device of FIG. 1.

FIG. 2 is a block diagram of an illustrative embodiment of the remote IMD 16 of FIG. 1. As shown in FIG. 2, the remote IMD 16 includes an energy storage device 56, a physiological sensor 58, an acoustic switch 60 (including the acoustic transducer 46, a signal detector 62, and an activation/deactivation switch component 64), power control circuitry 66, and a controller 68. The energy storage device 56 may be non-rechargeable or rechargeable, and operates to supply power to the physiological sensor 58, the acoustic switch 60, the power control circuitry 66, and the controller 68. The power control circuitry 66 is operatively connected to the acoustic switch 60, and is used to regulate the supply of power from the energy storage device 56 to the physiological sensor 58 and the controller 68.

The physiological sensor 58 performs functions related to the measurement of one or more physiological parameters within the body. In certain embodiments, for example, the physiological sensor 58 comprises a pressure sensor adapted to measure blood pressure in a body vessel. In one such embodiment, the remote IMD 16 is implanted in a pulmonary artery of the patient, and the physiological sensor 58 is adapted to sense arterial blood pressure. An example remote IMD 16 suitable for sensing blood pressure within an artery is described, for example, in U.S. Provisional Patent Application No. 61/060,877, entitled "Implantable Pressure Sensor with Automatic Measurement and Storage Capabilities," which is expressly incorporated herein by reference in its entirety for all purposes. In other embodiments, the physiological sensor 58 is adapted to generate a signal related to other sensed physiological parameters including, but not limited to, temperature, electrical impedance, position, strain, pH, blood flow, radiation level, and glucose level. In some embodiments, the remote IMD 16 may also include a therapy delivery module 70 that performs one or more therapeutic functions (e.g., cardiac pacing, drug delivery) within the body in addition to, or in lieu of, the one or more sensing functions provided by the physiological sensor 58.

The acoustic transducer 46 for the remote IMD 16 may include one or more piezoelectric transducer elements configured to transmit and receive acoustic signals. In a reception mode of operation, the acoustic transducer 46 is configured to receive the acoustic signal 44,52 transmitted from the external device and/or the pulse generator 14, which is fed to the controller 68 when the remote IMD 16 is in the active state. The acoustic transducer 46, or another acoustic transducer coupled to the remote IMD 16, is configured to transmit an outward acoustic signal 71 to the external device 12 and/or the pulse generator 14. The transmitted acoustic signal 71 can include sensor data obtained from the physiological sensor 58, information relating to the status or operation of the remote IMD 16 (e.g., power status, communication mode status, error correction information, etc.), as well as other information relating to the operation of the remote IMD 16.

The signal detector 62 is configured to generate an activation trigger signal to activate the remote IMD 16 via the activation/deactivation switch component 64. The activation trigger signal is generated by the signal detector 62 when the electrical signal generated by the acoustic transducer 46 exceeds a specific voltage threshold. The activation/deactivation switch component 64 is the component through which current is delivered from the energy storage device 56 to the controller 68 when actuated.

In response to the generation of the activation trigger signal by the signal detector 62, the switch component 64 is actuated to allow current to flow to the controller 68, thereby placing the remote IMD 16 in the active state. The switch component 64 can also be actuated to prevent current from flowing to the controller 68, thereby placing the remote IMD 16 in the standby state. Further details regarding the general construction and function of acoustic switches are disclosed in U.S. Pat. No. 6,628,989, entitled "Acoustic Switch And Apparatus And Methods For Using Acoustic Switches Within The Body," which is expressly incorporated herein by reference in its entirety for all purposes. In other embodiments, the external device 12 or the pulse generator 14 operates to generate a field (i.e., a wake-up field) that can be detected by a sensing module in the remote IMD 16 for the purpose of causing the remote IMD 16 to wake from the sleep state. For example, the remote IMD 16 can include an antenna or inductive coil that receives an RF or inductive signal from the external device 12 or pulse generator 14 to wirelessly activate or deactivate the remote IMD 16 within the body.

The controller 68 includes a processor 72 such as a microprocessor or microcontroller coupled to a memory device 74 that includes operating instructions and/or software for the remote IMD 16. The controller 70 also includes an oscillator or other timing circuitry 76 which directs the timing of activities performed by the remote IMD 16 once awoken from its low-power or sleep state. For example, the timing circuitry 76 can be used for timing the physiologic measurements taken by the physiological sensor 58, and to generate timing markers to be associated with those measurements. The controller 68, including the processor 72, can be configured as a digital signal processor (DSP), a field programmable gate array (FPGA), an application specific integrated circuit (ASIC)-compatible device, and/or any other hardware components or software modules for processing, analyzing, storing data, and controlling the operation of the remote IMD 16.

The processor 72 can be configured to analyze, interpret, and/or process the received acoustic signals 44,52 as well as the signals received by the physiological sensor 58. As discussed further herein with respect to FIGS. 4-6, the processor 72 is configured to run an adaptation algorithm or routine 78 that analyzes the performance of the acoustic link between the remote IMD 16 and the external device 12 and/or pulse generator 14, and responsive to such feedback, adjusts one or more operating parameters of the remote IMD 16 to ensure that the acoustic link is adequately maintained. A similar controller may be provided on the pulse generator 14 to permit the pulse generator 14 to measure an acoustic link established between the remote IMD 16 and the pulse generator, and responsive to such feedback, adjust one or more operating parameters of the pulse generator 14, if desired.

Figure 3:
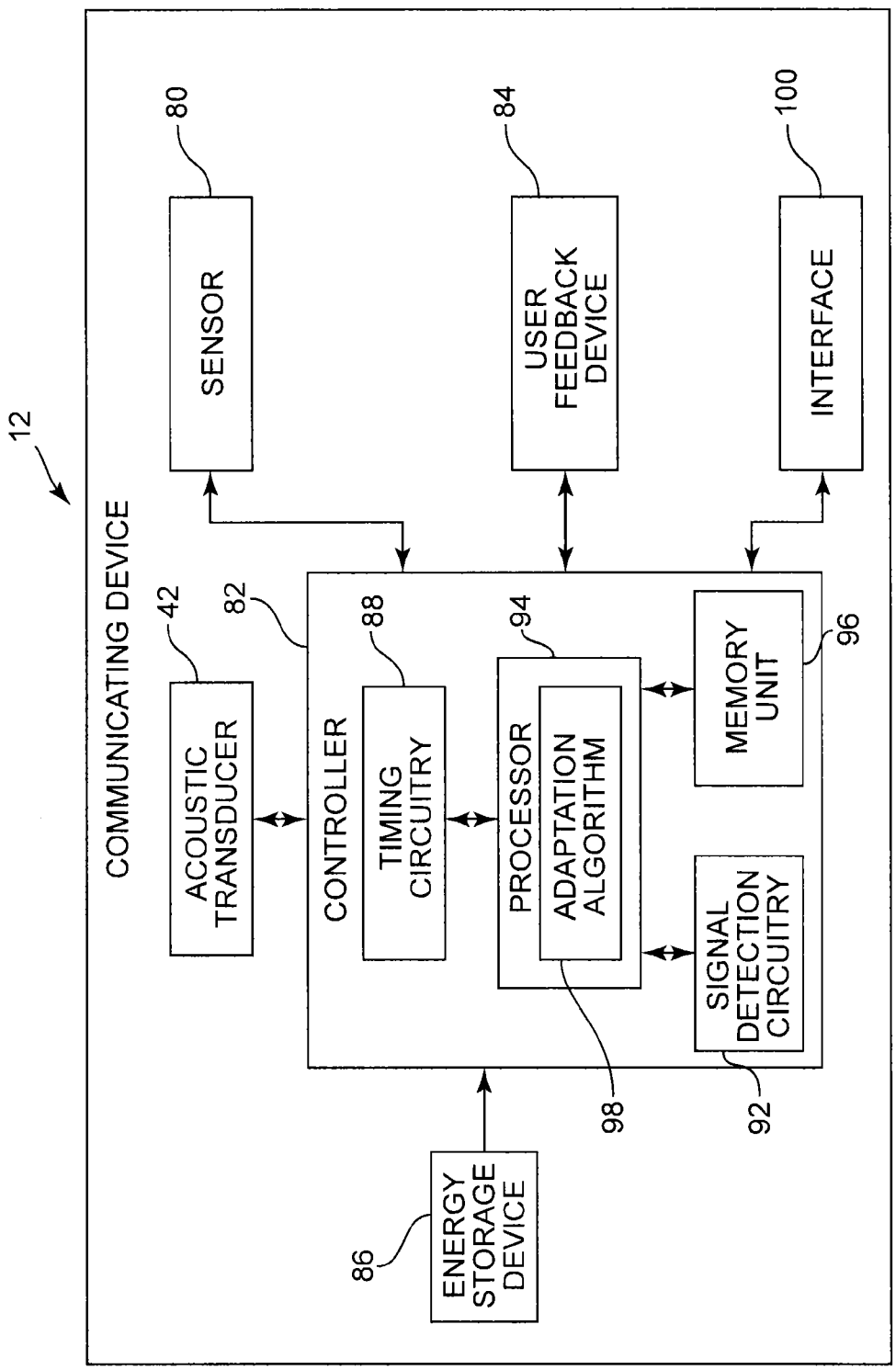
FIG. 3 is a block diagram of an illustrative embodiment of the external device of FIG. 1.

FIG. 3 is a block diagram of an illustrative embodiment of the external device 12 of FIG. 1. As shown in FIG. 3, the external device 16 includes an acoustic transducer 42, an on-board sensor 80, a controller 82, a user feedback device 84, and an energy storage device 86. In some embodiments, the external device 12 is a handheld device. In other embodiments, the external device 12 is attached to a portion of the patient's body such as the patient's arm, neck, chest, thigh, or knee. The external device 12 can use any type of attachment mechanism, such as a strap, a patch, a belt, or any other means for coupling the device 12 to the patient's body.

The sensor 80 may comprise a biosensor that generates a signal in response to a sensed physiological parameter. In one embodiment, for example, the sensor 80 comprises a barometric pressure sensor configured to measure barometric pressure for use in calibrating a pressure signal received from the remote IMD 16. The external device 12 may include one or more additional sensors such as an ECG electrode sensor, a systemic blood pressure sensor, a posture sensor, a global positioning system (GPS) sensor, an activity sensor, a temperature sensor, a timer, and/or an oximeter.

The acoustic transducer 42 for the external device 12 is configured to both transmit and receive acoustic signals to and from the pulse generator 14 and remote IMD 16. In other embodiments, the external device 12 includes at least one transducer configured for receiving acoustic signals and at least one transducer for transmitting acoustic signals. The acoustic transducer 42 generates an electrical signal proportional to the magnitude of acoustic energy received by the transducer 42, which is then conveyed to the controller 82. In similar fashion, the acoustic transducer 42 generates an acoustic signal proportional to the magnitude of the electrical energy generated by the controller 82.

The controller 82 includes circuitry for activating or controlling the sensor 80 and for receiving signals from the sensor 80. In some embodiments, the controller 82 may include an oscillator or other timing circuitry 88 for use in modulating the acoustic signal transmitted to the remote IMD 16 and/or the pulse generator 14 via the acoustic transducer 42. The controller 82 can also include signal detection circuitry 92 for detecting acoustic signals received from the remote IMD 16 and/or the pulse generator 14 via the acoustic transducer 42.

The controller 82 includes a processor 94 for analyzing, interpreting, and/or processing the received acoustic signals, and a memory 96 for storing the processed information and/or commands for use internally. In certain embodiments, for example, the processor 94 can be used to analyze the strength and quality of the acoustic signal received from the remote IMD 16 and/or the pulse generator 14. The controller 82, including the processor 94, can be configured as a digital signal processor (DSP), a field programmable gate array (FPGA), an application specific integrated circuit (ASIC)-compatible device, and/or any other hardware components or software modules for processing, analyzing, storing data, and controlling the operation of the external device 12. During operation, and as discussed further herein, the processor 94 can be configured to run an algorithm or routine 98 that analyzes the performance of the acoustic link between the external device 12 and the remote IMD 16 and/or the pulse generator 14, and responsive to such feedback, adjusts one or more operating parameters of the external device 12 to ensure that the acoustic link is adequately maintained.

The user feedback device 84 can include a screen or display panel for communicating information to a clinician and/or to the patient. For example, the screen or display panel can display information indicative of the strength and/or quality of the acoustic signal received from the remote IMD 16 and/or from the pulse generator 14. The user feedback device 84 can also be configured to display information relating to various operating parameters and status information of the external device 12, the remote IMD 16, and/or the pulse generator 14. For example, the user feedback device 84 can display information regarding the transmission power or intensity of the acoustic signal 44 transmitted to the remote IMD 16, the frequency of the transmitted acoustic signal 44, and the modulation format of the transmitted acoustic signal 44 (e.g., pulse code modulation (PCM), frequency shift keying (FSK), frequency modulation (FM), or amplitude modulation (AM)). The user feedback device 84 can also display other information regarding the acoustic signal 44, including the occurrence of any communication errors that may have occurred.

The user feedback device 84 can also display information regarding the operation of the remote IMD 16 and/or the pulse generator 14, including the transmission power or intensity of the acoustic signal 71 transmitted by the acoustic transducer 46 for the remote IMD 16, the carrier frequency of the acoustic signal 71 transmitted by the acoustic transducer 46, the bit/word timing and word resolution of the acoustic signal 71 transmitted by the acoustic transducer 46, and the sampling rate or word size of the acoustic signal 71 transmitted by the acoustic transducer 46. In certain embodiments, the user feedback device 84 can also be used to display other information such as any physiological parameters sensed by the remote IMD 16, the power status of the remote IMD 16, and the operating status of the pulse generator 14.

In some embodiments, the external device 12 can include an interface 100 for connecting the device 12 to the Internet, an intranet connection, to a cell phone, and/or to other wired or wireless means for downloading or uploading information and programs, debugging data, and upgrades. According to some embodiments, the external device 12 may also be capable of operating in two modes: a user mode that provides useful clinical information to the patient or a caregiver, and a diagnostic mode that provides information to an individual for calibrating and/or servicing the external device 12 or for changing one or more parameters of the remote IMD 16 and/or pulse generator 14.

Figure 4:
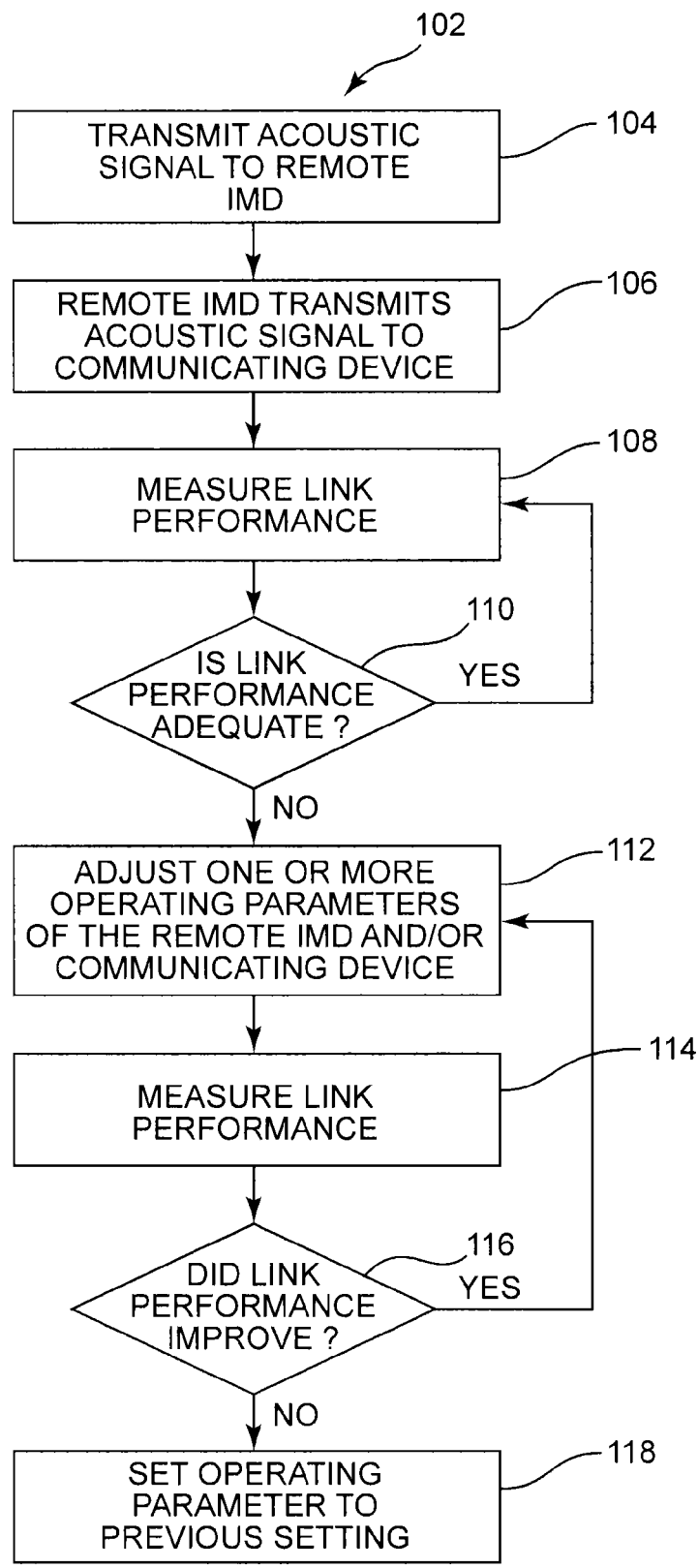
FIG. 4 is a flow chart showing an illustrative method of adapting an acoustic communication link with an implantable medical device.

FIG. 4 is a flow chart showing an illustrative method 102 of adapting an acoustic link with an implantable medical device. The method 102 may comprise, for example, a method of adapting an acoustic communication link between an external device 12 and a remote IMD 16, or alternatively, between a pulse generator 14 and a remote IMD 16. The method 102 may also be used to adapt an acoustic communication link between the remote IMD 16 and another device implanted within the body.

The method 102 may begin generally with the step of establishing an acoustic link between the remote IMD 16 and another communicating device such as the external device 12 and/or the pulse generator 14. To initiate the acoustic link, the external device 12 or pulse generator 14 transmits an acoustic signal to the remote IMD 16 (block 104). Upon receiving the acoustic signal, the remote IMD 16 enters into a transmission mode of operation and transmits an acoustic signal back to the external device 12 or pulse generator 14 (block 106) that can then be used to measure the performance of the acoustic link between the two communicating devices (block 108). If, for example, the remote IMD 16 receives an acoustic signal from the external device 12, the IMD 16 transmits an acoustic signal back to the external device 12 that can be used by the external device 12 to measure the performance of the acoustic link between the remote IMD 16 and the external device 12.

In certain embodiments, the performance of the individual acoustic paths within one or more acoustic links can also be measured. For example, the performance measuring step (block 108) can include measuring the performance of an acoustic link established when the external device 12 is the receiver and the remote IMD 16 is the transmitter. In addition, the external device 12 may individually measure the acoustic link performance when the external device 12 is the transmitter and the remote IMD 16 is the receiver. Any performance of other communication path(s) between the external device 12, the remote IMD 16, and/or one or more additional IMDs may also be measured.

The performance of the acoustic link can be measured in a number of different ways. In certain embodiments, for example, the performance of the acoustic link can be measured by determining the number of communication errors or timeouts that occur over a period of time, and then comparing that number against a predetermined threshold stored in a look-up table. The performance of the acoustic link can also be determined by measuring the intensity of the acoustic signal and then comparing the measured intensity level against a predetermined threshold intensity level. Other means for measuring the performance of the acoustic link are also possible. For example, the performance of the acoustic link can be determined by reducing the transmitter power of the remote IMD 16, increasing the receiver threshold of the external device 12 and/or pulse generator 16, and/or by varying the clock frequency.

Based on the measured performance of the acoustic link (block 108), the external device 12 next determines whether the acoustic link established between the two communicating devices is adequate based on the current operating parameters (block 110). The determination of whether the acoustic link is adequate can be accomplished, for example, using the controller 82 for the external device 12. Alternatively, and in other embodiments, the determination of whether the acoustic link is adequate can be accomplished by the controller 68 for the remote IMD 16. In some embodiments, both of the controllers 68,82 can be configured to assess the performance of the acoustic link.

If at block 110 the performance of the acoustic link is adequate, the remote IMD 16 and external device 12 continue to operate using their current operating parameters. Otherwise, if at block 110 the performance of the acoustic link is inadequate, the external device 12 may adjust one or more operating parameters of the remote IMD 16 and/or the external device 12 in order to improve the link performance (block 112). Example operating parameters that can be adjusted to improve link performance can include, but are not limited to, increasing the transmission power or intensity of the acoustic signal transmitted by the remote IMD 16, increasing the receiving sensitivity or thresholds of the acoustic transducer 42 for the external device 12, adjusting the transmission frequency of the acoustic signal transmitted by the remote IMD 16, increasing the bit or word timing of the acoustic signal transmitted by the remote IMD 16, increasing the sampling rate or word size of the acoustic signal transmitted by the remote IMD 16, and/or changing the duty cycle of the bits transmitted by the remote IMD 16.

Once one or more operating parameters associated with the acoustic link are adjusted (block 112), the external device 12 and/or remote IMD 16 may then measure the performance of the acoustic link using the adjusted operating parameter(s) (block 114). For example, if the power or intensity of the acoustic signal transmitted by the remote IMD 16 is increased, the external device 12 may ascertain whether the performance of the acoustic link improved over the previous power or intensity setting (block 116). If at block 116 the performance of the acoustic link improves using the previous, adjusted operating parameter, the external device 12 and/or remote IMD 16 may repeat the process of adjusting the operating parameter (block 112) (e.g., by a step function) and then measuring the performance of the acoustic link (block 114) in response to that adjusted operating parameter. The process of adjusting the operating parameters may be repeated one or more times until, at block 116, the adjusted operating parameter does not improve the performance of the acoustic link. If, for example, an adjustment in the power or intensity of the acoustic signal does not result in an improvement in the performance of the acoustic link, the remote IMD 16 may then set the current power or intensity setting to the prior setting. The method 102 may then be repeated one or more times, either automatically by the remote IMD 16 and/or the communicating device 12,14, or manually via a request from a user or process.

Figure 5:
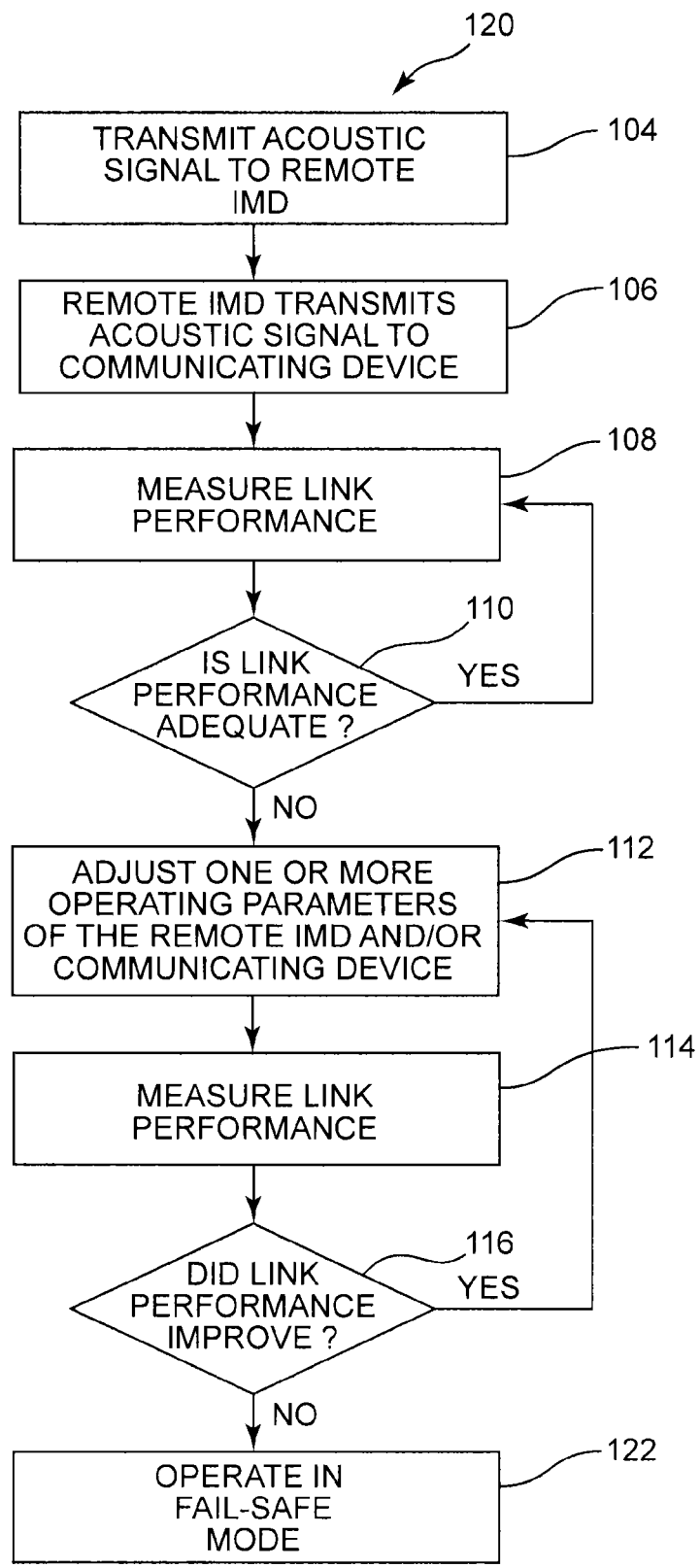
FIG. 5 is a flow chart showing another illustrative method of adapting an acoustic communication link with an implantable medical device.

FIG. 5 is a flow chart showing another illustrative method 120 of adapting an acoustic link with an implantable medical device. Method 120 is similar to the method 102 of FIG. 4, but further includes the step (block 122) of operating the remote IMD 16 in a fail-safe mode of operation in the event the performance of the acoustic link is not improved upon a change in the previous operating setting, and when the prior operating setting was inadequate to maintain the link performance. In some embodiments, for example, the fail-safe mode can be initiated if no other adjustment in operating parameter was successful in restoring the acoustic link to an acceptable performance level. In the fail-safe mode, the remote IMD 16 may sacrifice certain performance criteria such as speed or power usage to assure that an acceptable level of performance or other criteria (e.g., reliability, availability, etc.) is maintained.

In some embodiments, the fail-safe mode may include an auto-transmit mode to improve the performance of the communication link. In certain embodiments, for example, the auto-transmit mode can be initiated within the remote IMD 16 if the external device 12 receives ten commands in a row from the remote IMD 16 and/or the pulse generator 14 with communication errors. When this occurs, the remote IMD 16 may initiate the auto-transmit mode and transmit a data package having a fixed timing pattern such that the communicating device 12,14 can determine the remote IMD's 16 oscillator rate and adjust its oscillator rate accordingly. The remote IMD 16 can also be configured to transmit other parameters as part of the data package, including the pulse width and amplitude of the acoustic signal.

Figure 6:
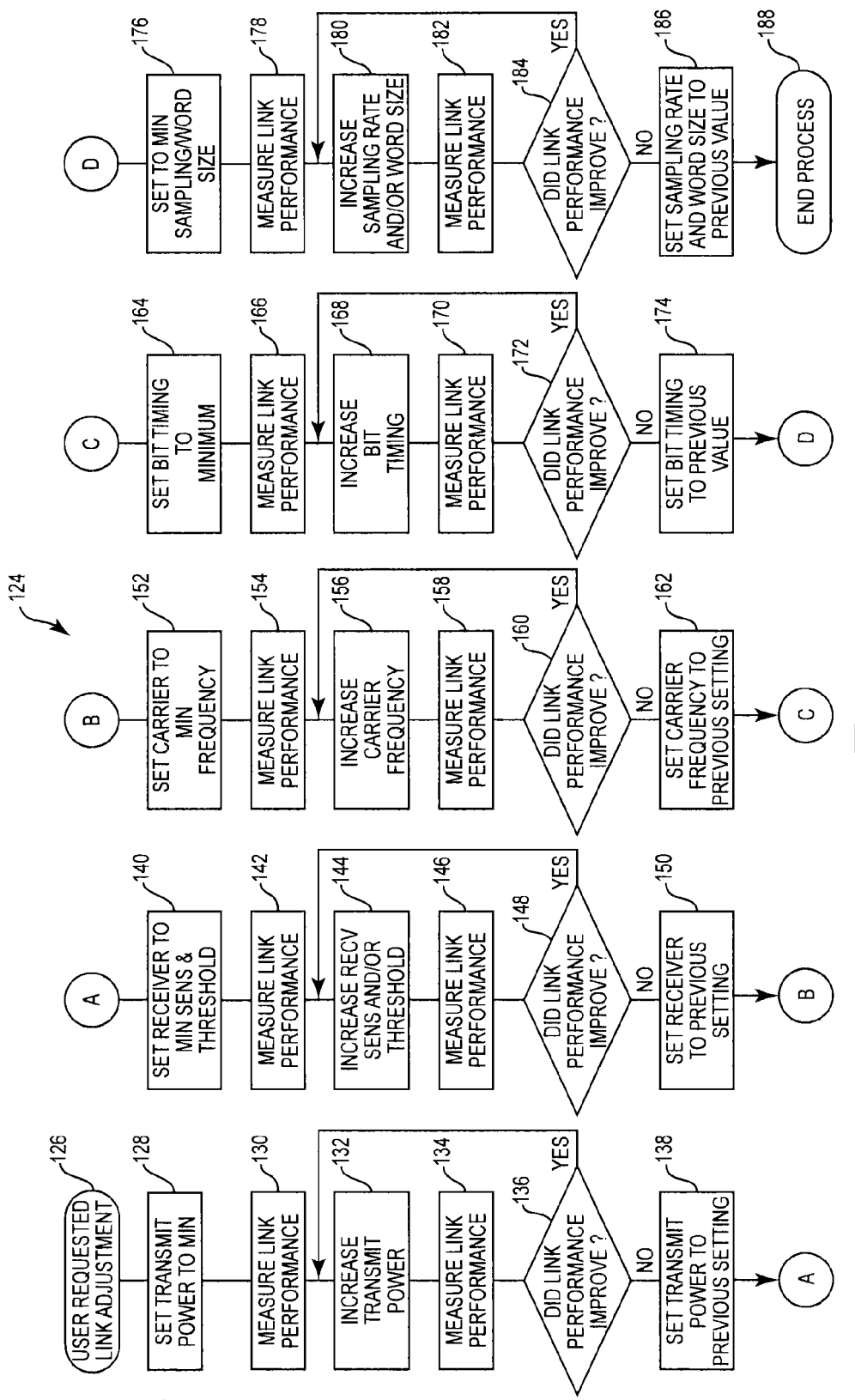
FIG. 6 is a flow chart showing an illustrative implementation of the method of FIG. 4.

FIG. 6 is a flow chart showing another illustrative method 124 of adapting an acoustic communication link with an implantable medical device. As shown in FIG. 6, the method 124 may be initiated in response to a request by a user (block 126). In some embodiments, for example, the link adjustment may be initiated manually by a caregiver or patient entering a command into an interface device (e.g., the user feedback device 84) in response to an alarm or warning indicating that an error in the communications has occurred. Alternatively, and in other embodiments, the link adjustment may be initiated automatically by the remote IMD 16, or by a signal from a communicating device 12,14, to resolve any problems in the link availability, power efficiency, and/or data reliability. In certain embodiments, for example, the method 124 may be initiated automatically when the performance of the acoustic link drops below a predetermined threshold level.

Once initiated, the remote IMD 16 can be configured to set one or more operating parameters at an initial value, and then stepwise increase each operating parameter in order to improve the performance of the acoustic link between the remote IMD 16 and the communicating device. In the embodiment of FIG. 6, for example, the remote IMD 16 may initially set the transmission power of the acoustic signal provided by acoustic transducer 46 to a minimum level (block 128). Using this minimum transmission power, the performance of the acoustic transmission is then measured (block 130) at this minimum level. The transmission power is then increased to a higher level (block 132), and the performance of the acoustic transmission is again measured at the new transmission level to determine whether the increase in transmission power improves the link performance (block 134). If at decision block 136 the performance of the link improves, the remote IMD 16 increases the power transmission level to a higher level (block 132) and again measures the link performance (block 134) at this new value to determine whether the link performance further improves. The process of increasing the transmit power and measuring the link performance at each increase can be repeated one or more times until, at such point, the link performance does not improve, or until a maximum transmission threshold value programmed within the remote IMD 16 is achieved. At this point, the remote IMD 16 may then set the transmission power to the last setting that resulted in an increase in the link performance (block 138).

One or more other operating parameters may be adjusted in a similar manner in order to further improve the performance of the acoustic link between the remote IMD 16 and the external device 12 and/or pulse generator 14. In some embodiments, for example, the external device 12 can be configured to initially set the receiving acoustic transducer to a minimum sensitivity or threshold (block 140). Using this minimum receiver sensitivity or threshold, the external device 12 then measures the performance of the acoustic transmission at this minimum level (block 142). The receiver sensitivity is increased and/or the threshold decreased (block 144), and the performance of the acoustic link is again measured to determine whether the performance has improved (block 146). If at decision block 148 the performance of the link improves, the external device 12 may repeat the process of increasing the sensitivity or threshold level (block 144) and measuring the link performance (block 146) at this new sensitivity or threshold level to determine whether the link performance further improves. The process may then be repeated one or more times until, at such point, the link performance does not improve, or a maximum sensitivity or threshold value is achieved. The external device 12 may then set the receiver sensitivity or threshold value to the previous setting that resulted in an increase in the link performance (block 150).

The carrier frequency used to modulate the acoustic signal transmitted by the remote IMD 16 can be further adjusted to increase the performance of the acoustic link. In some embodiments, for example, the carrier frequency for the remote IMD 16 can be initially set to a minimum frequency (block 152). Using this minimum carrier frequency, the external device 12 then measures the performance of the acoustic transmission at this minimum level (block 154). The carrier frequency is then increased to a higher frequency (block 156), and the performance of the acoustic link is again measured at the increased frequency to determine whether the link performance improved (block 158). If at decision block 160 the performance of the link improves, the process of increasing the carrier frequency (block 156) and measuring the link performance (block 158) at the new carrier frequency is repeated. Otherwise, if the performance does not improve, the remote IMD 16 may set the carrier frequency to the last frequency that resulted in an increase in the link performance (block 162).

The bit timing of the acoustic signal, representing the timing between successive bits or words in the acoustic signal, can be further adjusted to increase the performance of the acoustic link. The bit timing may represent, for example, factors such as the data rate, pulse width, and the bit or word interval of the data stream transmitted as part of the acoustic signal. The remote IMD 16 initially sets the bit timing to a minimum value (block 164), which is then analyzed by the external device 12 and/or pulse generator 14 in order to measure the performance of the acoustic transmission using the minimum bit timing (block 166). The bit timing is then increased to a higher rate (block 168), and the performance of the acoustic link is again measured at the increased bit rate to determine whether the link performance improved (block 170). If at decision block 172 the performance of the link improves, the process of increasing the bit timing (block 168) and measuring the link performance (170) at the new bit timing value is repeated. Otherwise, if the performance does not improve, the remote IMD 16 may set the bit timing value to the last value that resulted in an increase in the link performance (block 174).

The sampling rate or word resolution can be further adjusted to increase the performance of the acoustic link. The remote IMD 16 initially sets the sampling rate or word resolution to a minimum value (block 176). Using this minimum value, the external device 12 then measures the performance of the acoustic link at this minimum level (block 178). The sampling rate or word resolution is then increased to a higher rate or resolution (block 180), and the performance of the acoustic link is again measured at the increased rate or resolution to determine whether the link performance improves (block 182). If at decision block 184 the performance of the link improves, the process of increasing the sampling rate or word resolution (block 180) and measuring the link performance (block 182) at the new rate or resolution is repeated. Otherwise, if the performance does not improve, the remote IMD 16 may set the sampling rate or word resolution to the previous value that resulted in an increase in the link performance (block 186). As indicated generally at block 188, once one or more of operating parameters associated with the acoustic link have been adjusted, the remote IMD 16 may then terminate the algorithm and await another user request (block 126) to initiate the method 124.

The ordering of the operating parameters that are adjusted may differ from that shown in the illustrative method 124 of FIG. 6. In some embodiments, only operating parameters associated with the transmission of the acoustic signal by the remote IMD 16 are adjusted to improve the performance of the acoustic link. In other embodiments, only operating parameters associated with the reception of the acoustic signal by the external device 12 and/or pulse generator 14 are adjusted to improve the link performance.

In addition, although FIG. 6 depicts several illustrative operating parameters that can be adjusted in order to improve link performance, in other embodiments other types of operating parameters can also be adjusted in a similar fashion. In some embodiments, for example, the modulation format (e.g., PCM, FSK, FM, AM, etc.) of the acoustic signal transmitted by the remote IMD 16 can be adjusted in order to improve link performance. In one such embodiment, for example, the remote IMD 16 may switch from one modulation format (e.g., FSK) to a second, different modulation format (e.g., FM) in order to increase the bandwidth of the acoustic signal. The remote IMD 16 can also be configured to adjust the type of error correction employed to detect communications errors, including type-based error checking and correction (e.g., parity, cyclic redundancy check (CRC), etc.) and interval-based error checking and correction (e.g., bit, word, block, etc.). For example, the remote IMD 16 can be configured to switch from a relatively low-level error checking technique (e.g., parity error detection) to a relatively high-level error checking technique (e.g., CRC) in the event greater error checking and correction is required to maintain the acoustic link.

In certain embodiments, the antenna gain or directionality of the acoustic transmission can be adjusted in order to improve the performance of the acoustic link. In one such embodiment, the acoustic transducer 42 for the external device 12 and/or the acoustic transducer 46 for the remote IMD 16 may include a phased-array of ultrasonic transducer elements. To improve the directionality of the acoustic transmission, phase delay adjustments can be provided on one or more of the ultrasonic elements within the array in order to manipulate the acoustic transmission through the body. By adjusting the directionality of the acoustic transmission, a greater portion of the acoustic signal can be received by the external device 12 and/or the pulse generator 14, thus increasing the performance of the acoustic link.

The transmission frequency of the acoustic signal can also be adjusted in order to improve the performance of the acoustic link. In one such embodiment, the frequency of the transmitted acoustic signal can be adjusted by sweeping the frequency of the acoustic signal across a range of frequencies, and at each frequency or at multiple, discrete frequencies, measuring the power or intensity of the acoustic signal. The operation frequency can then be set at a frequency that produces the acoustic signal with the greatest power or intensity.

In certain embodiments, the method 124 can be configured to adjust one or more operating parameters of the remote IMD 16 in order to maintain a minimally acceptable performance of the acoustic link. If, for example, the current operating parameter is determined by the controller 68 to be sufficient to establish an adequate acoustic communication link between the remote IMD 16 and the receiver, the method 124 may continue to operate using the current parameter until, at such point, further adjustment to the parameter is necessary to maintain the acoustic link. With respect to the step of measuring the link performance (block 134) in response to the current transmit power setting, for example, the controller 68 may conclude that the current transmit power setting is sufficient to maintain a minimal level of performance, and thus continue operation using this setting until the performance of the acoustic link falls below a threshold value. Maintaining the operating parameter at this minimum threshold level may be useful, for example, for limiting the amount of acoustic exposure the patient receives while still maintaining an adequate link with the receiver. Maintaining the operating parameter at this minimum threshold may also be used to conserve power consumption from the energy storage device 56 as well as computational resources from the controller 68.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system, comprising:
an implantable medical device configured to transmit and receive wireless signals;
a communicating device in wireless communication with the implantable medical device via a wireless link;
a processor configured to:
measure at least one performance parameter of the wireless link;
adjust at least one operating parameter of the implantable medical device or the communicating device from a first operating parameter setting to a second operating parameter setting, in response to the at least one measured performance parameter;
determine whether adjusting the at least one operating parameter improves a performance of the wireless link by analyzing a change in the performance of the wireless link in response to adjusting the at least one operating parameter; and
set the at least one operating parameter to the first operating parameter setting if adjusting the operating parameter does not improve the performance of the wireless link.

2. The system of claim 1, wherein, in adjusting at least one operating parameter of the implantable medical device or communicating device, the processor is configured to stepwise increase the at least one operating parameter over a range of parameter values.

3. The system of claim 1, wherein operating parameter includes at least one of a transmission power parameter, a receiver sensitivity parameter, a receiver threshold parameter, a carrier frequency parameter, a transmission frequency parameter, a bit timing parameter, a sampling rate parameter, a bit word size parameter, and a modulation format parameter.

4. The system of claim 1, wherein the implantable medical device includes a therapy delivery module.

5. The system of claim 4, wherein the implantable medical device comprises a pacing device.

6. The system of claim 4, wherein the implantable medical device comprises a drug delivery device.

7. The system of claim 1, wherein the implantable medical device further includes a sensing module.

8. The system of claim 1, wherein the communicating device is an external device.

9. The system of claim 1, wherein the communicating device is an implantable device.

10. The system of claim 1, wherein the communicating device is an implantable pulse generator.

11. A wireless pacing system for delivering therapy to a body, the system comprising:
a wireless pacer configured for delivering electrical therapy to the body, the wireless pacer configured to transmit and receive wireless signals;
a communicating device in wireless communication with the wireless pacer via a wireless link;
a processor configured for measuring at least one performance parameter of the wireless link and adjusting at least one operating parameter of the wireless pacer or the communicating device from a first operating parameter setting to a second operating parameter setting, in response to the at least one measured performance parameter, wherein the processor is further configured for:
- determining whether adjusting the at least one operating parameter improves a performance of the wireless link, wherein said determining comprises analyzing a change in the performance of the wireless link in response to adjusting the at least one operating parameter; and
- setting the at least one operating parameter to the first operating parameter setting if adjusting the operating parameter does not improve the performance of the wireless link.

12. The system of claim 11, wherein, in adjusting at least one operating parameter of the implantable medical device or communicating device, the processor is configured to stepwise increase the at least one operating parameter over a range of values.

13. The system of claim 11, wherein operating parameter includes at least one of a transmission power parameter, a receiver sensitivity parameter, a receiver threshold parameter, a carrier frequency parameter, a transmission frequency parameter, a bit timing parameter, a sampling rate parameter, a bit word size parameter, and a modulation format parameter.

14. The system of claim 11, wherein the wireless pacer further includes a sensing module.

15. The system of claim 11, wherein the communicating device is an external device.

16. The system of claim 11, wherein the communicating device is an implantable pulse generator.

17. A wireless pacing system for delivering therapy to a body, the system comprising:
- a wireless pacer configured for delivering electrical therapy to a body, the wireless pacer configured to transmit and receive wireless signals;
- a communicating device in wireless communication with the wireless pacer via a wireless link;
- a means for measuring at least one performance parameter of the wireless link;
- a means for adjusting an operating parameter of the wireless pacer or the communicating device from a first operating parameter setting to a second operating parameter setting, in response to the at least one measured performance parameter; and
- a means for determining whether adjusting the at least one operating parameter improves a performance of the wireless link, said means for determining whether adjusting the at least one operating parameter improves a performance of the wireless link including a means for analyzing a change in the performance of the wireless link in response to adjusting the operating parameter, wherein the means for adjusting the operating parameter sets the at least one operating parameter to the first operating parameter setting if adjusting the operating parameter does not improve the performance of the wireless link.

* * * * *